United States Patent [19]

Hashino et al.

[11] 4,267,053

[45] May 12, 1981

[54] INLINE INTRAVENOUS FINAL FILTER UNIT

[75] Inventors: Yasuo Hashino; Fusakazu Hayano, both of Fuji; Kazuo Toyomoto, Yokohama, all of Japan

[73] Assignees: Asahi Kasei Kogyo Kabushiki Kaisha; Morishita Pharm., both of Osaka, Japan

[21] Appl. No.: 50,444

[22] Filed: Jun. 20, 1979

Related U.S. Application Data

[63] Continuation of Ser. No. 837,208, Sep. 27, 1977, abandoned.

[30] Foreign Application Priority Data

Oct. 15, 1976 [JP] Japan ................... 51-122876

[51] Int. Cl.³ ................... B01D 29/32; B01D 31/00
[52] U.S. Cl. ................... 210/650; 210/446; 210/321.1; 210/323.2; 210/433.2
[58] Field of Search ....... 210/321 R, 433 M, 445-448, 210/450, 490, 500 M, 23 F, 323 T; 264/177

[56] References Cited

U.S. PATENT DOCUMENTS

| | | | |
|---|---|---|---|
| 2,675,000 | 4/1954 | Ford | 210/448 X |
| 2,704,544 | 3/1955 | Ryan | 128/214 R |
| 2,879,784 | 3/1959 | Cutter | 210/448 X |
| 3,471,019 | 10/1969 | Trasen et al. | 210/94 |
| 3,612,282 | 10/1971 | Cheng | 210/433 M X |
| 3,760,949 | 9/1973 | Carey et al. | 210/450 X |
| 3,970,084 | 7/1976 | Raines et al. | 210/94 X |
| 3,978,857 | 9/1976 | McPhee | 210/446 X |

FOREIGN PATENT DOCUMENTS

| | | |
|---|---|---|
| 2236226 | 2/1974 | Fed. Rep. of Germany . |
| 1077115 | 11/1954 | France . |
| 1546081 | 11/1968 | France . |
| 2265437 | 10/1975 | France . |
| 717733 | 11/1954 | United Kingdom . |
| 751436 | 6/1956 | United Kingdom . |

OTHER PUBLICATIONS

Robert Rapp et al.; "Evaluation of a Prototype Air Venting Inline Intravenous Filter Set", 1975; American Journal of Hospital Pharmacy, pp. 1253-1259, Dec. 1975.

*Primary Examiner*—Robert H. Spitzer
*Attorney, Agent, or Firm*—Oblon, Fisher, Spivak, McClelland & Maier

[57] ABSTRACT

An inline intravenous final filter unit especially of the bacteria-retentive type and adapted to be incorporated in administering sets for administering infusion solutions to patients. The filter unit comprises a casing having an inlet cap at its one end and an outlet cap at the other end thereof, at least one porous hollow fiber arranged within the casing in parallel to the longitudinal direction thereof and having a porosity rating of 0.1 to 5µ, the hollow fiber being closed at its one end opposed to the inlet cap and open at the other end thereof opposed to the outlet cap, the hollow fiber further being tightly fixed at the outer peripheral portion of its open end to the inner wall of the casing by a securing member, and the ratio of the total effective filtration area of the hollow fiber to the capacity of the casing being at least about 4:1.

10 Claims, 6 Drawing Figures

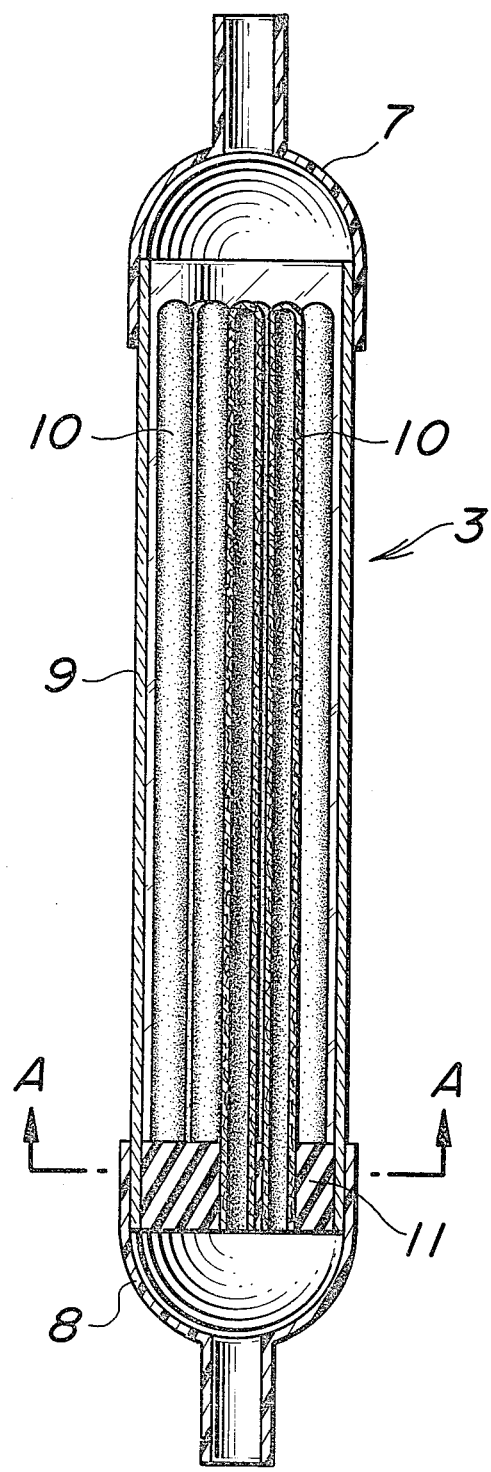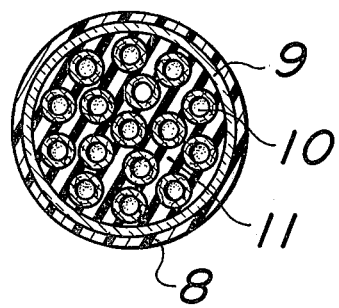

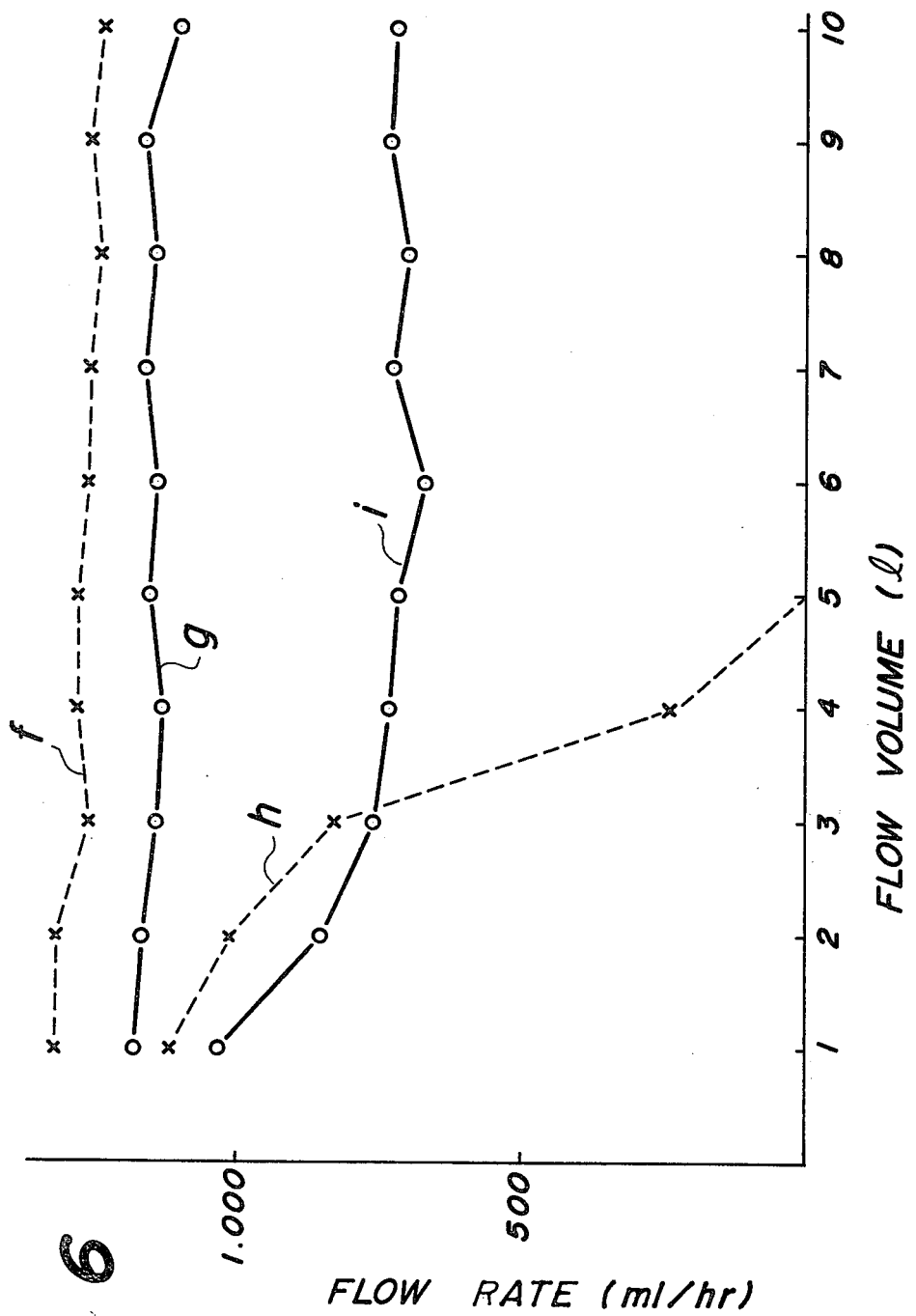

INLINE INTRAVENOUS FINAL FILTER UNIT

This is a continuation, of application Ser. No. 837,208, filed Sept. 27, 1977, now abandoned.

BACKGROUND OF THE INVENTION

1. Field of the Invention

This invention relates to intravenous solution administering sets for administering infusion solutions such as lactated Ringer's, dextrose, amino acids and hyperalimentation solutions to patients, and in particular to improvements in an inline intravenous final filter unit especially of the bacteria-retentive type adapted to be incorporated in such a set.

2. Description of the Prior Art

At present various infusion solutions are administered to patients for nourishment, adjustment of the electrolyte balance in the body, supplementation of water and therapy. When water or nutriment is parenterally supplemented, the adult requires about 2 l/day of water. This quantity is equivalent to four 500 ml vials. Such large quantities of infusion solutions may be given continually for a prolonged period of time depending on the condition of the patient. These combined quantities will then be 100 l or more. If such a large amount of infusion solution is injected into the body of the patient, very small quantities of fine particles contained in the solution will be accumulated in the body, enhancing the likelihood that the fine particles will cause disorders. In fact, it has been pointed out that fine particles, when introduced into the human body, are liable to cause capillary obstruction, granuloma, damage to cells and necrosis, further aggravating progressive tumor or inducing cancer.

With the development of hyperalimentation solution thereby in recent years, there arises the necessity of using infusion solution administering devices equipped with a final filter unit which is capable of removing bacteria and fungi as well as fine particles by filtration. According to this therapy, an infusion solution incorporating a hypertonic sugar-amino acids mixture, an electrolyte solution and vitamins is administered to the patient at a constant rate over a prolonged period of time through a catheter inserted into the subclavien vein to give the patient the required nourishment, water, etc. solely with the solution. It is therefore critical that the passage for the solution be provided with a final filter unit for removing bacteria and fungi for the prevention of bacterial contamination and candidiasis.

Inline intravenous final filter units are already known in the art. More specifically, Japanese Patent Application Disclosures No. 23286/1973, No. 103890/1975, No. 96089/1975, No. 103487/1974 and No. 1586/1975 disclose such filter units including a cloth bag filter, a filter of fibrous adsorbent coated with a tacky oil and packed into a layer, a filter of randomly arranged material and packed into a layer, a porous metal filter and a filter made from sintered product of fine stainless steel particles, respectively. However, these filter units are all adapted to remove fine particles only from the infusion solution and are unable to remove bacteria.

U.S. Pat. No. 3,471,019 and No. 3,978,857 disclose membrane filter units having a porosity rating of about 0.2 to about $0.5\mu$. Of these units, those having a porosity rating of $0.22\mu$, although absolutely bacteria-retentive, do not have a sufficient surface area to provide adequate flow rates with a gravity feed system. Such a filter, if used, necessitates a positive pressure infusion pump to maintain flow rates.

SUMMARY OF THE INVENTION

Accordingly, an object of this invention is to provide a novel inline intravenous final filter unit which is capable of completely removing bacterial and fungi as well as fine particles from the infusion solution and which has a large filtration area to provide sufficient flow rates merely with a gravity feed system but without necessitating a positive pressure infusion pump.

Another object of this invention is to provide a final filter unit which is hydrodynamically so designed as to maintain appropriate and constant flow rates over a long period of time for use with infusion solutions containing a drug additive having particulate matter, such as solutions containing an antibiotic additive, without entailing a hazardous clogging problem while filtering the solution.

Another object of this invention is to provide a final filter unit which is extremely compact, inexpensive and well suited to disposable use.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIGS. 2 to 3 are enlarged views in section showing an embodiment of the filter unit of the invention; and FIGS. 4 to 6 are diagrams showing the results of solution flow tests conducted with use of the filter unit of the invention.

DETAILED DESCRIPTION OF THE PREFERRED EMBODIMENTS

Figure 1:
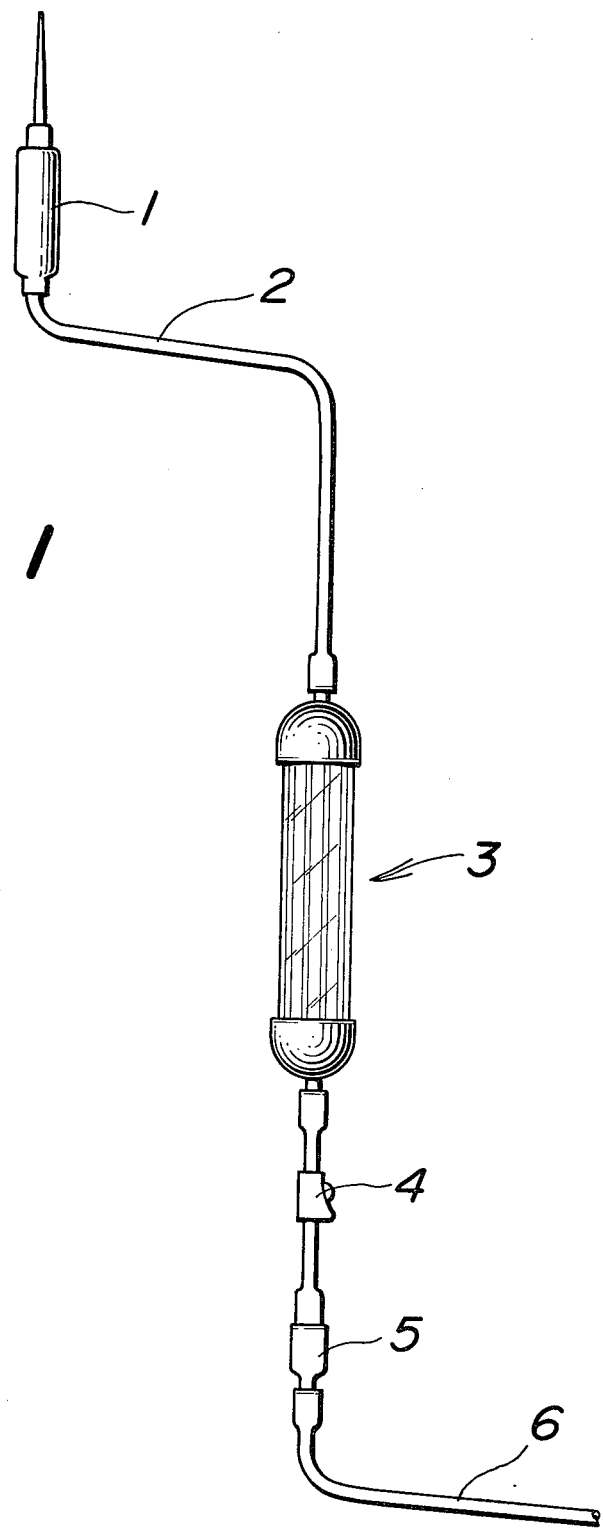
FIG. 1 is a view showing an intravenous solution administering set incorporating an inline intravenous final filter unit of this invention.

With reference to the drawings, FIG. 1 shows an intravenous solution administering set incorporating a filter unit of this invention. The administering set comprises a member 1 for withdrawing the solution from an infusion bottle, a conduit tube 2, a filter unit 3, a flow rate regulator 4, a needle or catheter connector 5 and a catheter 6 in combination. In place of the catheter 6, an infusion needle may of course be fitted to the connector 5.

This invention relates to the special final filter unit 3, an embodiment of which is shown in FIG. 2 or 3 on an enlarged scale. The filter unit 3 includes a hollow cylindrical casing 9 having an inlet cap 7 at its one end and an outlet cap 8 at the other end thereof, and porous hollow fibers 10 arranged in parallel within the casing 9 and extending longitudinally thereof. Each of the porous hollow fibers 10 is closed at its one end opposed to the inlet cap 7 and open at the other end opposed to the outlet cap 8. The outer peripheral portion of the open end of the hollow fiber 10 is tightly fixed to the inner wall of the casing 9 with a securing member 11 of suitable material such as silicone resin.

Examples of useful materials for forming the porous hollow fibers of this invention are usually cellulose acetates such as cellulose diacetate and cellulose triacetate. Also useful are other polymeric materials which can be formed into fibers, such as nitrocellulose, polyvinyl chloride, polyacrylonitrile, etc. The process per se for producing porous hollow fibers having varying pore size distributions is already known in the fiber industry as disclosed for example in Japanese Patent Application Disclosure No. 93786/1976. For instance, porous hollow fibers of cellulose acetate are produced by preparing a solution of cellulose acetate polymer in a suitable solvent having no affinity for the polymer and extruding the solution from annular spinning nozzle into a hot atmosphere. One end of each of the hollow fibers is closed by heat sealing or with a silicone adhesive.

The wall membranes of the hollow fibers thus obtained have a reticular structure provided by numerous fine pores with a porosity of 80 to 90%. Accordingly even if some pores become clogged up during filtration, the solution flows through the other pores without entailing an abrupt decrease in the flow rate of the filtrate. The hollow fibers useful in this invention have a porosity rating of 0.1 to 5μ. The preferred porosity rating for the removal of bacteria and fungi is 0.1 to 0.5μ. Preferably the hollow fibers have an outside diameter of up to 3 mm; over 3 mm, the fibers will be collapsed by suction or pressure. The fibers are at least 0.5 mm in inside diameter and preferably 1 to 10 cm in length. If less than 1 cm in length, the fibers will have too small an effective filtration area, whereas in excess of 10 cm, the fibers are difficult to handle for assembly. When a plurality of hollow fibers are used, use of about 5 to about 30 fibers favors the assembling procedure.

The casing of the filter unit of this invention, although not particularly limited in shape, is generally in the form of a hollow cylinder 4 to 20 mm in inside diameter and 1 to 12 cm in length and is made from polyethylene, polyvinyl chloride, polypropylene, polystyrene or the like.

To sum up, the characteristic design features of the present filter unit are as follows. The hollow fibers having a porosity rating of 0.1 to 0.5μ used as filter elements filter off fine particles and various bacteria and fungi contained in infusion solutions but must fulfill another requirement. The flow rates required of the infusion solutions to be administered to patients are dependent on the kind of the solution as well as on the therapeutic purpose and are about 500 ml/h for solutions such as lactated Ringer's, 5% glucose or dextrose and 9.12% amino acid mixture solutions and 80 to 100 ml/h for hyperalimentation solutions. Such flow rates must be achieved solely by gravity feed without using a positive infusion pump.

We have found that this requirement can be successfully fulfilled by two design factors; first by arranging the filter elements, namely, the hollow fibers 10, within the casing longitudinally of the casing so as to minimize the resistance to the flow of the solution, and second by adapting the hollow fibers arranged within the casing to have a total effective filtration area, A, of 5–100 cm², preferably, 20–60 cm² and an A/V ratio of at least about 4 in which V is the capacity in cm³ of the casing.

The filter unit of this invention incorporating these design factors has the advantages of being extremely compact as compared with conventional units and substantially free of the clogging of the filter element inevitably caused in the prior art by the particulate matter present in the solution. For instance, the conventional membrane-type filter units are up to about 1.3, if highest, in A/V ratio which generally appears indicative of the compactness of filter units. Quite unexpectedly, the filter unit of this invention operates without entailing any significant clogging of the filter elements despite the presence of particulate matter in the solution. Presumably this is attributable partly to the fact that because the hollow fibers are arranged in parallel within the casing lengthwise of the casing, the flow of the solution through the fibers takes place not at right angles but with a sufficient inclination with respect to the wall membranes of the fibers, consequently making it difficult for particles to closely accumulate on the membranes.

Other characteristic features and advantages of this invention will become more apparent from the test example to follow.

TEST EXAMPLE

A filter unit as shown in FIG. 2 was prepared in which sixteen porous hollow fibers 0.5 mm in inside diameter, 1.4 mm in outside diameter, 60 mm in length and 0.32μ in porosity rating were accommodated in a hollow cylindrical casing 8 mm in inside diameter, 10 mm in outside diameter and 80 mm in length and tightly secured to the inner wall of the casing by securing member made of a silicone-type adhesive material. The filter unit had a filtration area, A, of 35.2 cm² and an A/V ratio of 5.61. The porous hollow fibers were made from cellulose diacetate, and the casing, inlet cap and outlet cap from polyethylene.

The filter unit was incorporated into an infusion solution administering set as shown in FIG. 1 and tested as follows.

1. Removal of fine particles and bacteria (1) A dispersion containing 0.4μ particles of latex dispersed therein was diluted with water to a concentration of 0.05%, and the dilute dispersion was passed through the administering set. The liquid flowing out from the set was found to be completely free from the latex particles.

(2) Distilled water was filtered by a membrane filter 0.22μ in porosity rating, placed into an infusion bottle and sterilized at 20° C. for 20 minutes. *Serratia marcescens* was added in a bacterial count of $10^5$–$10^6$/ml to the sterilized water, the water was then passed through the administering set, and a 5 ml portion of the liquid flowing out from the set was placed into a culture tube and maintained for one week for culture. When thereafter checked, the liquid was found free from any bacteria.

2. Filtration rate and viscosity of infusion solutions

The filter unit was treated for filtration rate and the viscosity of the solution with use of lactated Ringer's solution (trademark: "EL-H," product of Morishita Seiyaku Co., Ltd., Japan), 5% glucose solution (product of Morishita), 9.12% amino acid mixture (trademark: "MORIAMIN-S," product of Morishita), hyperalimentation solution (21% dextrose plus 3.3% amino acid mixture) and mixture of 1.52% amino acid mixture, 6% dextran and 5% sorbitol (trademark: "MORIAMIN D-2," product of Morishita). The test was conducted with the solution inlet of the filter unit positioned 1 m below the outlet of the bottle.

| | Solution | Flow rate ml/h | Flow rate ml/cm² . h | Viscosity* (c.p.) |
|---|---|---|---|---|
| a. | Lactated Ringer's | 1,179 | 33.5 | 0.82 |
| b. | 5% Glucose | 981 | 27.9 | 1.07 |

-continued

| Solution | Flow rate ml/h | ml/cm². h | Viscosity* (c.p.) |
|---|---|---|---|
| c. 9.12% Amino acid mixture | 752 | 21.4 | 1.20 |
| d. Hyperalimentation | 573 | 16.3 | 2.05 |
| e. 6% Dextran + 5% sorbitol + 1.52% amino acid mixture | 198 | 5.6 | 4.08 |

*measured at 20° C., by PHEOMATIS (CONTRAVES CO., LTD.)

Figure 4:
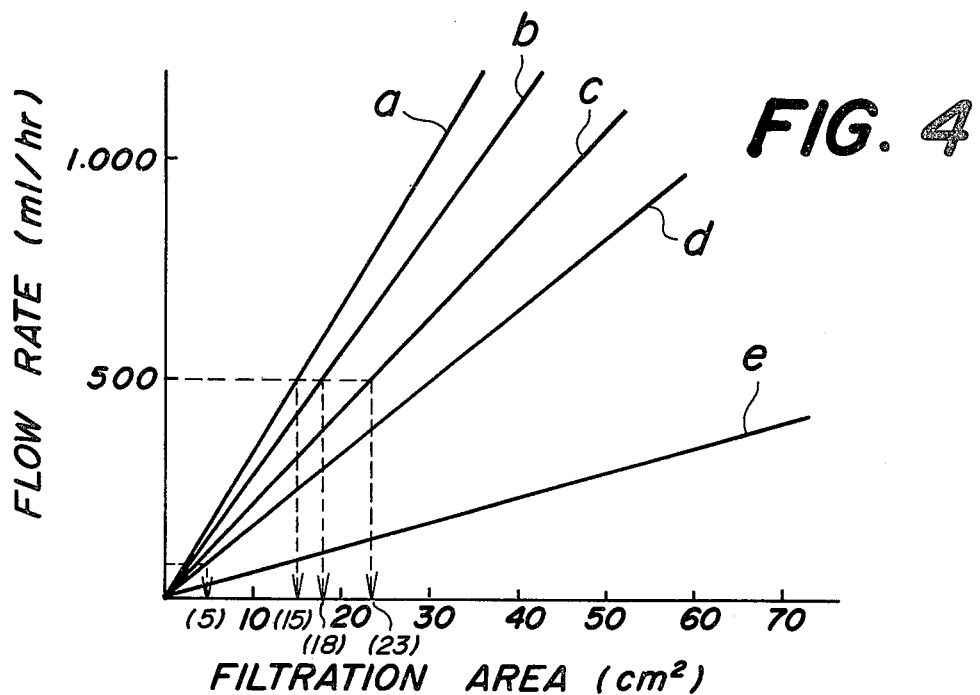
Figure 5:
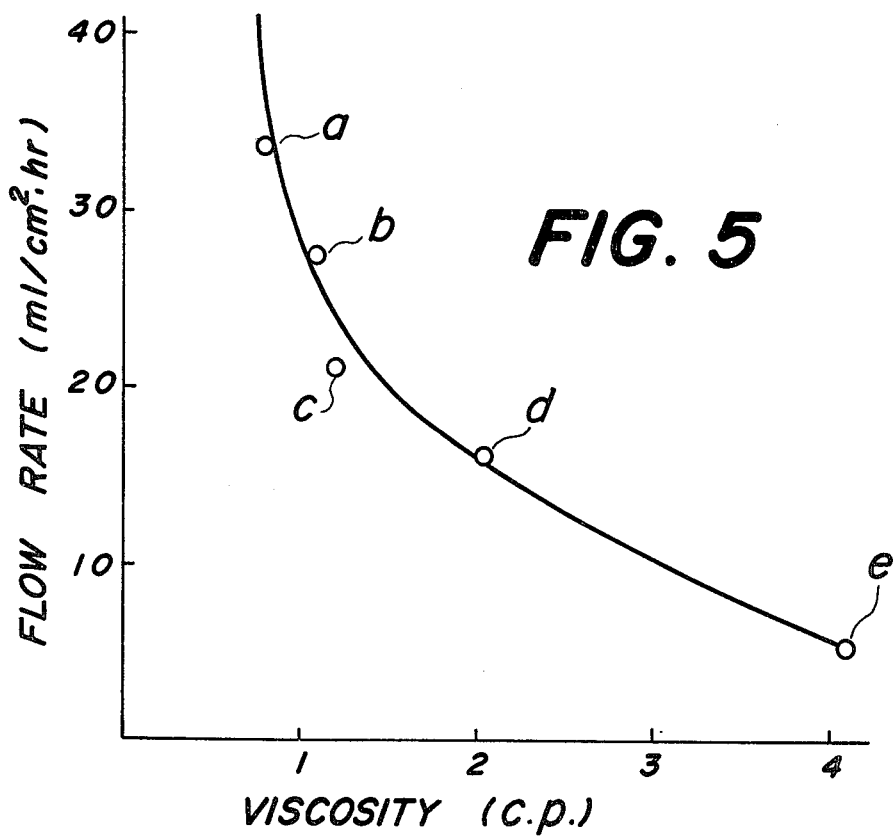

FIG. 4 shows the relationship between the flow rate and the effective filtration area determined from the above results, and FIG. 5 the relationship between the viscosity of the solution and the flow rate per unit effective filtration area.

3. Clogging of filter

The administering set of this invention and an administering set of the membrane type filter unit (0.45μ in porosity rating and 25 mm in diameter of membrane filter) were tested for flow rate with use of lactated Ringer's solution with and without addition of ampicillin (1 g/liter) thereto. The flow rate (ml/h) was calculated from the time taken for a volume of 50 ml filtered as measured upon every increment of 1 liter in the cumulative volume of the filtrate. The results are given in FIG. 6 for comparison between the two filter units, wherein curves f (Reference) and g (Present Invention) indicate the results without addition of ampicillin while curves i (Present Invention) and h (Reference) indicate the results with addition of ampicillin.

Obviously, numerous modifications and variations of the present invention are possible in light of the above teachings. It is therefore to be understood that within the scope of the appended claims, the invention may be practiced otherwise than as specifically described herein.

What is claimed is:

1. A method for removing bacteria and fungi from an infusion solution in an inline intravenous final filter unit which includes a casing having an inlet at one end and an outlet at the other end thereof which comprises:

arranging a plurality of hollow fibers within the casing, each of said hollow fibers having an outside diameter of up to 3 mm, an inside diameter of at least 0.5 mm, a porous size of 0.1μ to 0.5μ and a porosity of 80% to 90% with the hollow fibers being opened at at least one end thereof;

fixing a security member to each end of said hollow fibers so as to connect said hollow fibers to each other and to abut the inner wall of the casing such that the final filter unit has a total effective filtration area of 5–100 cm² wherein the ratio of the total effective filtration area to the capacity of the casing is at least about 4:1; and filtering the solution through said inline intravenous final filter unit.

2. A method as set forth in claim 1 which further comprises dimensioning said hollow fibers so as to be 1 cm to 10 cm in length.

3. A method as set forth in claim 1, which further comprises arranging 5 to 30 hollow fibers within said casing such that said hollow fibers have a total effective filtration area of 20 cm² to 60 cm².

4. A method as set forth in claim 1, said hollow fibers comprising cellulose acetates.

5. An inline intravenous final filter unit including a casing having an inlet cap at its one end and an outlet cap at the other end thereof, a plurality of tubed filter elements arranged within the casing parallel to the longitudinal direction thereof, each of said tubed filter elements being closed at one end thereof opposed to the inlet cap and open at the other end thereof opposed to the outlet cap and a securing member for tightly fixing each of said tubed filter elements at the outer peripheral portion of each open end thereof to the inner wall of the casing wherein each of said tubed filter elements comprises porous hollow fiber of up to 3 mm in outside diameter and at least 0.5 mm in inside diameter, said porous hollow fiber having a porosity of 80–90% so as to be free from clogging by particulate matter in infusion solutions, a porosity rating of 0.1–0.5μ so as to suitable for the removal of bacteria or fungi contaminated thereinto and including a total effective filtration area of 5–100 cm² and wherein the ratio of the total effective filtration area to the capacity of the casing is at least about 4:1.

6. A filter unit as defined in claim 5 wherein each of said tubed filter elements comprises a single layered porous hollow fiber.

7. A filter unit as defined in claim 5 wherein said hollow fiber is 1 to 10 cm in length.

8. A filter unit as defined in claim 5 wherein five to thirty hollow fibers are arranged within said casing, said hollow fibers having a total effective filtration area of 20 to 60 cm².

9. A filter unit as defined in claim 8 wherein said hollow fibers are made of cellulose acetate.

10. A filter unit as defined in claim 5 wherein the casing is made of polyethylene, polyvinyl chloride, polystyrene or polypropylene.

* * * * *